US00PP27942P2

(12) United States Plant Patent
Hartman

(10) Patent No.: US PP27,942 P2
(45) Date of Patent: Apr. 25, 2017

(54) ***CALADIUM* PLANT NAMED 'SOUTHERN CHARM'**

(50) Latin Name: *Caladium×hortulanum*
Varietal Denomination: Southern Charm

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 14/998,534

(22) Filed: Jan. 16, 2016

(51) Int. Cl.
*A01H 5/02* (2006.01)

(52) U.S. Cl.
USPC ..... Plt./373

(58) Field of Classification Search
USPC ..... Plt./373
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Caladium* plant named 'Southern Charm', characterized by its compact, short in height, upright and uniformly mounded plant habit when grown as a container plant; vigorous growth habit and rapid growth rate; and fancy-type leaves that are grey green in color with dark green-colored margins and red purple-colored venation and areas surrounding the venation.

4 Drawing Sheets

Botanical designation: *Caladium×hortulanum.*
Cultivar denomination: 'SOUTHERN CHARM'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Southern Charm'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2008 in Avon Park, Fla. of *Caladium×hortulanum* 'White Wonder', disclosed in U.S. Plant Pat. No. 21,044, as the female, or seed, parent with *Caladium×hortulanum* 'Blaze', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2009.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2010 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Southern Charm'. These characteristics in combination distinguish 'Southern Charm' as a new and distinct *Caladium* plant:

1. Compact, short in height, upright and uniformly mounded plant habit when grown as a container plant; plants are taller and more upright when grown under outdoor field conditions.
2. Vigorous growth habit and rapid growth rate.
3. Fancy-type leaves that are grey green in color with dark green-colored margins and red purple-colored venation and areas surrounding the venation.

Plants of the new *Caladium* differ primarily from plants of the female parent, 'White Wonder', in the following characteristics:

1. Plants of the new *Caladium* are shorter than plants of 'White Wonder'.
2. Plants of the new *Caladium* have fancy type leaves whereas plants of 'White Wonder' have strap (or lance) type leaves.
3. Plants of the new *Caladium* and 'White Wonder' differ in leaf color as leaves of 'White Wonder' are white to grey-green in color with light pink to white-colored venation and dark green-colored borders.
4. Plants of the new *Caladium* and 'White Wonder' differ in leaf petiole color as leaf petioles of 'White Wonder' are tan green in color with darker-colored stippling and stripes.

Plants of the new *Caladium* differ primarily from plants of the male parent, 'Blaze', in the following characteristics:

1. Plants of the new *Caladium* are more compact than plants of 'Blaze'.
2. Plants of the new *Caladium* and 'Blaze' differ in leaf color as leaves of 'Blaze' are dark green in color with burgundy red-colored venation and centers.

Plants of the new *Caladium* can be compared to plants of *Caladium×hortulanum* 'White Queen', not patented. In side-by-side comparisons, plants of the new *Caladium* differ primarily from plants of 'White Queen' in the following characteristics:

1. Plants of the new *Caladium* are more compact than plants of 'White Queen'.
2. Plants of the new *Caladium* and 'White Queen' differ in leaf color as leaves of 'White Queen' are white in color with rose pink-colored venation and central areas surrounding the venation.

Plants of the new *Caladium* can be compared to plants of *Caladium×hortulanum* 'Fantasy', not patented. In side-by-side comparisons, plants of the new *Caladium* differ primarily from plants of 'Fantasy' in the following characteristics:

1. Plants of the new *Caladium* are more compact than plants of 'Fantasy'.
2. Plants of the new *Caladium* and 'Fantasy' differ in leaf color as leaves of plants of 'Fantasy' are white in color with rose pink-colored centers and venation.
3. Plants of the new *Caladium* and 'Fantasy' differ in leaf petiole color as leaf petioles of 'Fantasy' are close to black in color.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Southern Charm' in a container and grown in a shadehouse (tuber not de-eyed).

The photograph at the top of the second sheet is a comparison view of typical potted plants of the female parent, 'White Wonder' (left), 'Southern Charm' (center) and the male parent, 'Blaze' (right).

The photograph at the bottom of the second sheet is a comparison view of typical potted plants of 'White Queen' (left), 'Southern Charm' (center) and 'Fantasy' (right).

The photograph at the top of the third sheet is a comparison view of typical plants of 'Southern Charm' grown in containers; the plant on the left has not had its tuber de-eyed and the plant on the right has had its tuber de-eyed prior to planting.

The photograph at the bottom of the third sheet is a side perspective view of typical plants of 'Southern Charm' grown in an open field.

The photograph at the top of the fourth sheet is a close-up view of typical freshly-harvested tubers and roots of 'Southern Charm'.

The photograph at the bottom of the fourth sheet is a close-up view of a typical inflorescence of 'Southern Charm'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were eight weeks old (vegetative plant photographs and description) and eleven weeks old (inflorescence photograph and description), and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Southern Charm'.

Parentage:

*Female, or seed, parent.*—*Caladium×hortulanum* 'White Wonder', disclosed in U.S. Plant Pat. No. 21,044.

*Male, or pollen, parent.*—*Caladium×hortulanum* 'Blaze', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented and somewhat flattened; individual segments ovate to irregular in shape. Height: About 3.5 cm. Diameter: About 4.3 cm to 5.3 cm. Segment height: About 2.2 cm. Segment diameter: About 2.2 cm to 2.4 cm. Axillary buds, height: About 6 mm. Texture: Thick, starchy. Color: Epidermis, freshly-harvested: Close to 159C variably tinged with close to 179D; outer skin, close to 199A to 199B. Epidermis, dried: Close to 200A. Cortical tissue: Close to 11C to 11D. Axillary buds: Close to N155C and 27D. Root description: Thick, fleshy contractile roots; color, close to 155C tinged with close to 49D. Rooting habit: Dense.

Plant description:

*Plant type.*—Herbaceous perennial; suitable as a potted plant in containers 15-cm to 25-cm and suitable as a landscape plant in shaded areas.

*Plant and growth habit.*—Compact, short in height, upright and uniformly mounded plant habit when grown as a container plant; plants are taller and more upright when grown under outdoor field conditions; vigorous and dense growth habit; rapid growth rate; potted plants in finished or saleable form in about eight weeks after planting tubers; leaf petioles and leaves arise from one or more growing points on tubers; petioles mostly upright and outwardly leaning with development.

*Plant height, from soil level to top of foliar plane, shadehouse-grown potted plants.*—About 17 cm to 23 cm.

*Plant height, from soil level to top of inflorescences, shadehouse-grown potted plants.*—About 38 cm.

*Plant diameter or spread, shadehouse-grown potted plants*.—About 27.5 cm to 38 cm.

*Number of shoots per plant, shadehouse-grown potted plants, tubers not de-eyed*.—About two to three develop per #1 tuber.

*Number of shoots per plant, shadehouse-grown potted plants, tubers de-eyed*.—About three to four develop per #1 tuber.

*Cataphylls, shadehouse-grown potted plants*.—Length: About 3.5 cm to 6 cm. Width: About 5 mm to 9 mm. Shape: Wedge-shaped. Apex: Acuminate or cuspidate. Base: Sheathing the stem. Color, inner surface: Close to N155C; colors and patterns on the outer surface are visible on the inner surface. Color, outer surface: Close to 147A and 147B variably streaked, stippled and tessellated with close to N186C; with development, color becoming closer to 200C to 200D stained with close to 187A.

Leaf description:

*Arrangement and type*.—Alternate; simple; fancy-type.

*Length, shadehouse-grown potted plants*.—About 12 cm to 18 cm.

*Width, shadehouse-grown potted plants*.—About 7.5 cm to 12.3 cm.

*Shape*.—Ovate to cordate.

*Apex*.—Acute to somewhat acuminate.

*Base*.—Sagittate to peltate.

*Margin*.—Entire; mostly flat with broad undulations.

*Texture, upper and lower surfaces*.—Smooth, glabrous; rigid.

*Luster, upper surface*.—Dull sheen.

*Luster, lower surface*.—Glaucous, dull sheen.

*Venation pattern*.—Pinnate.

*Color, shadehouse-grown potted plants*.—Developing leaves, upper surface: Background color: Close to 194D and close to 194D tinged with close to 184B; spots, close to 191C to 191D. Margins: Close to 147A to 147B. Basal notch: Close to 187A to 187B. Midvein and primary venation: Close to 187C. Lateral venation: Close to 147A. Areas surrounding venation: Close to between 184A and 187C. Developing leaves, lower surface: Background color: Close to 191A tinged with close to 189A, close to 191B tinged with close to 150D and close to 150D tinged with close to 191D; spots, close to 191D. Margins: Close to 147A to 147B. Midvein and primary venation: Close to 191A to 191B and close to 191A to 191B tinged with close to 177D. Lateral venation: Close to 189A. Areas surrounding venation: Close to 181A to 181B. Fully expanded leaves, upper surface: Background color: Close to 196A to 196B and close to 196A to 196B tinged with close to 184C. Margins: Close to 147A. Basal notch: Close to 187A. Midvein and primary venation: Close to between 187C and 53A. Lateral venation: Close to 147A tinged with close to 187C. Areas surrounding venation: Close to between 184B and 185B. Fully expanded leaves, lower surface: Background color: Close to 191B and close to 150D tinged with close to 191C. Margins: Close to 191A tinged with close to 189A. Main vein and primary venation: Close to 195B variably tinged with close to 184C and 181C. Lateral venation: Close to 137A. Areas surrounding venation: Close to 184B to 184C.

*Petioles*.—Aspect: Initially upright and straight; with development, leaning outwardly; relatively rigid. Length, shadehouse-grown potted plants: About 14 cm to 20 cm. Diameter, distally, shadehouse-grown potted plants: About 3.5 mm to 4 mm. Diameter, proximally, shadehouse-grown potted plants: About 6 mm to 10 mm. Texture: Smooth, glabrous; glaucous. Color, shadehouse-grown potted plants: Close to 147B and close to 147C variably tinged with close to 182C to 182D; below the leaf and petiole junction, close to 183B to 183C tinged and streaked with close to 147B or 147C to 147D. Wing length, shadehouse-grown potted plants: About 3.3 cm to 5.8 cm. Wing diameter, shadehouse-grown potted plants: About 7 mm. Texture, inner and outer surfaces: Smooth, glabrous. Luster, inner and outer surfaces: Dull to somewhat glossy. Wing color, shadehouse-grown potted plants: Inner surface: Close to N155C; colors and patterns on the outer surface are visible on the inner surface. Outer surface: Close to 147A and close to 147B variably streaked and stippled with close to N186C.

Inflorescence description: Inflorescences observed on eleven week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; sweet, jasmine-like with camphor note.

*Natural flowering season and flower longevity*.—Plants of the new *Caladium* typically flower during the spring in central Florida; flowers develop about eleven weeks after growth commences; inflorescences last about three days before fading; inflorescences persistent.

*Spathe*.—Length, overall: About 14.4 cm. Length, distal open portion: About 10 cm. Length, proximal closed portion: About 4.4 cm. Width, distal open portion: About 4.1 cm. Depth, distal open portion: About 3 cm. Width, at constriction: About 1.7 cm. Width, proximal closed portion: About 3.2 cm. Shape: Elliptic to obovate. Apex: Acuminate. Base: Obtuse. Margin: Entire; slightly reflexed. Texture, front and rear surfaces: Smooth, glabrous. Luster, front surface: Dull sheen. Luster, rear surface: Glaucous, dull sheen. Color, front surface: Distal open portion: Close to 155C; margins tinged with close to 157A; with development, color becoming closer to 200C. Proximal closed portion: Close to 148C to 148D, variably and faintly tinged with close to 181D; proximally, tinged and streaked with close to 187B; color does not change with development. Color, rear surface: Distal open portion: Close to 155D mottled with close to 145C to 145D; color does not change with development. Proximal closed portion: Close to 147B and 147D, mottled and streaked with close to 145C; margin, faintly tinged with close to 181C to 181D; color does not change with development.

*Spadix*.—Length, overall: About 9.1 cm. Length, male flower zone: About 5.5 cm. Length, sterile zone: About 1.4 cm. Length, female flower zone: About 2.2 cm. Diameter, male flower zone: About 1.1 cm. Diameter, sterile flower zone: About 9 mm. Diameter, female flower zone: About 1.2 cm. Shape: Columnar. Apex: Obtuse to bluntly acute. Base: Obtuse. Aspect: Upright. Color, mature, male zone: Close to 157D faintly tinged with close to 145C. Color, mature, sterile zone: Close to 155D. Color, mature, female zone: Close to 155C and 155A. Male flowers: Quantity per spadix: About 240. Shape: Obovate. Height: About 3 mm. Diameter: About 3 mm. Pollen amount: Abundant. Pollen color: Close to 11C. Female flowers: Quantity per spadix: About 250. Shape: Obovate. Height: About 3 mm. Diameter: About 1.5 mm to 2 mm. Stigma color: Close to 155C. Ovary color: Close to 155A.

*Scape*.—Length: About 23.6 cm. Diameter: About 9 mm. Strength: Sturdy; relatively rigid. Aspect: Mostly erect. Texture: Smooth, glabrous. Luster: Dull to slightly glossy; distally, slightly glaucous. Color: Close to 147C and 146D; just below spathe, close to 146D tinged with close to 147D.

*Seeds and fruits*.—To date, seed and fruit development have not been observed on plants of the new *Caladium*.

Disease & pest tolerance: Plants of the new *Caladium* have been observed to have average tolerance to *Xanthomonas* Leaf Spot and *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment overwinter for re-planting the following spring.

It is claimed:

1. A new and distinct *Caladium* plant named 'Southern Charm' as illustrated and described.

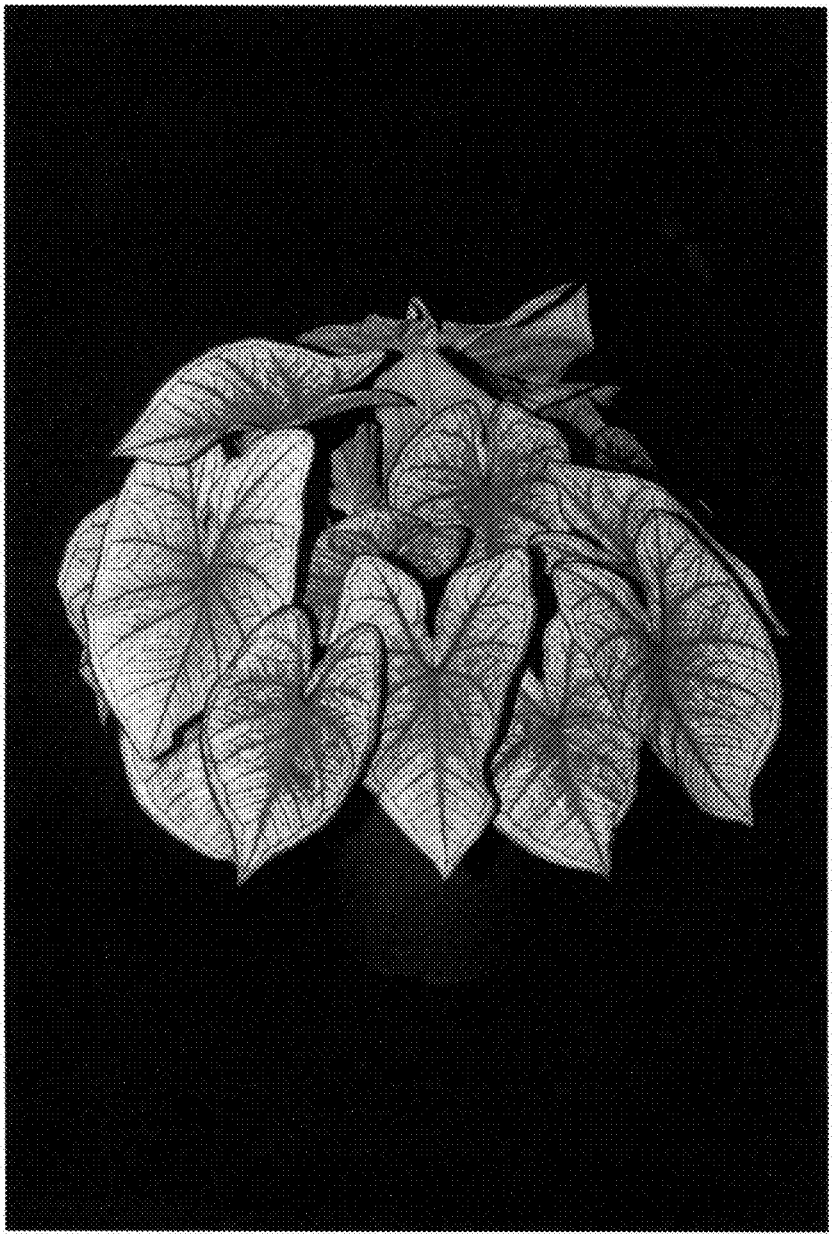

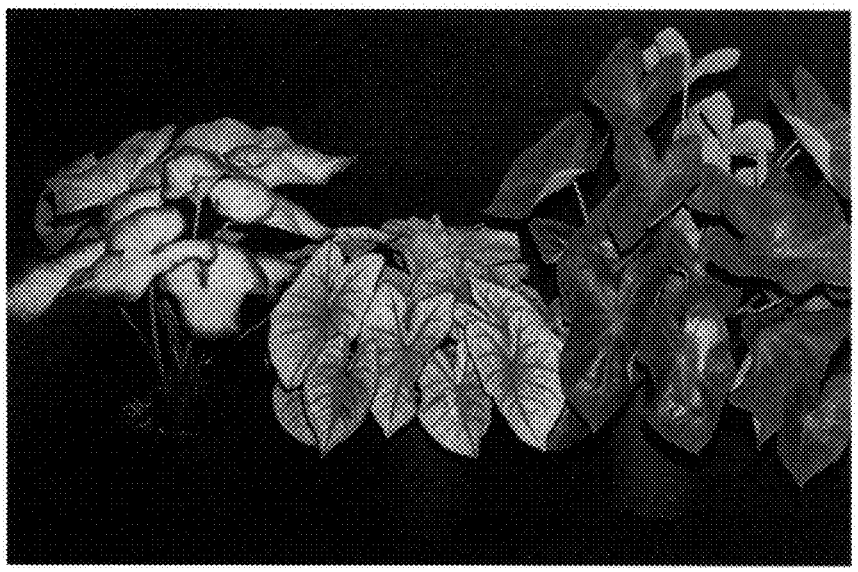
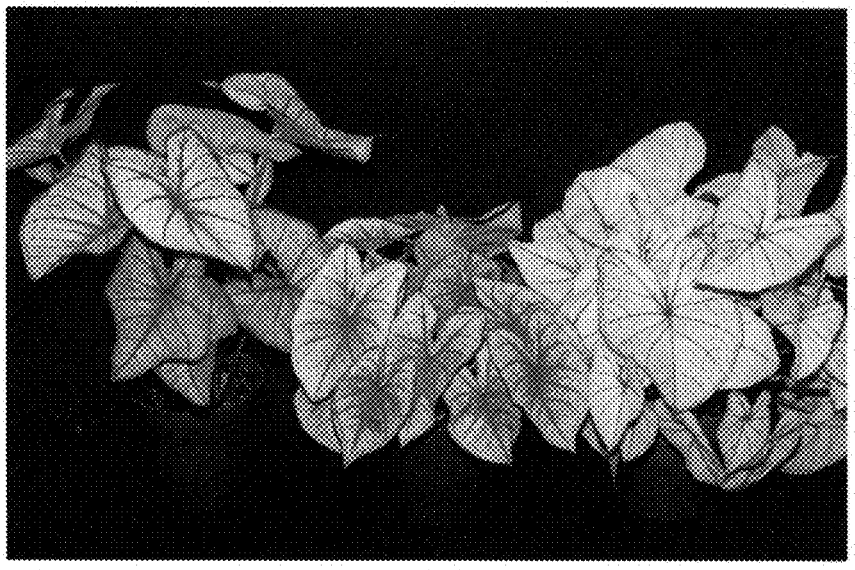

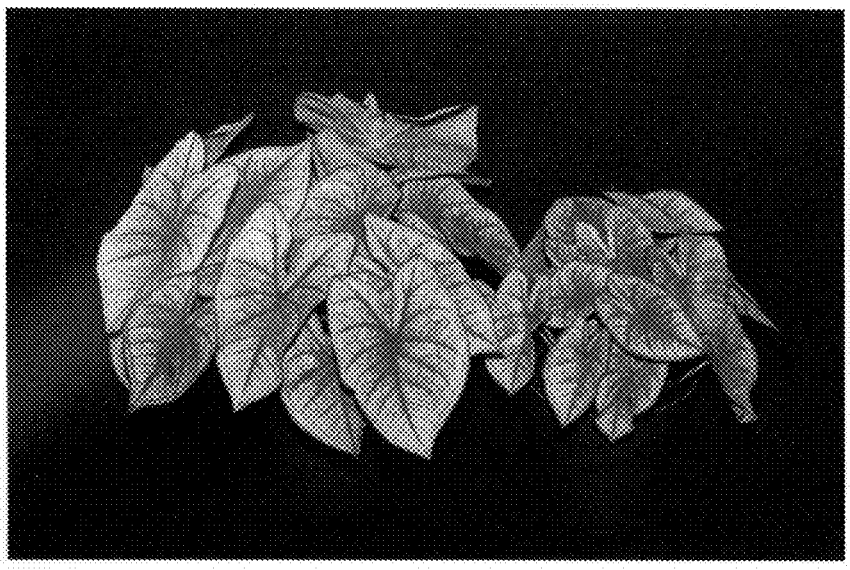
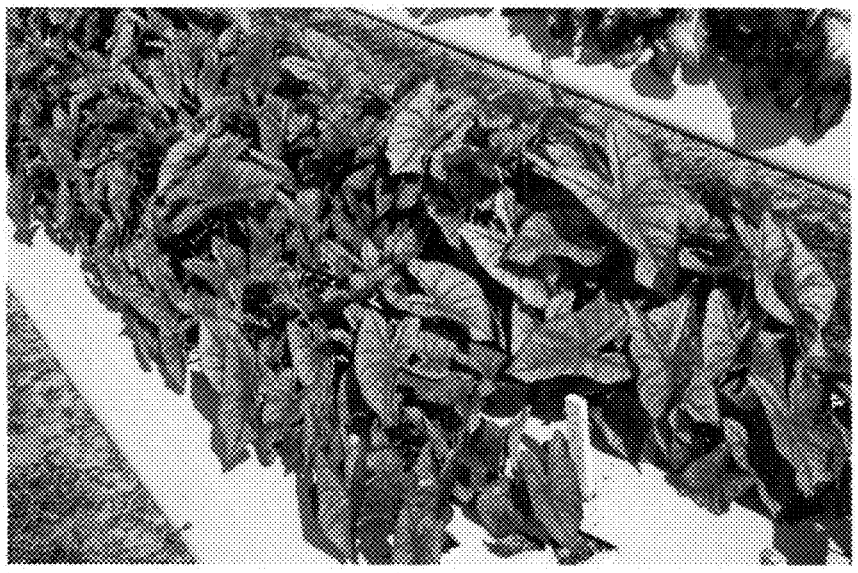

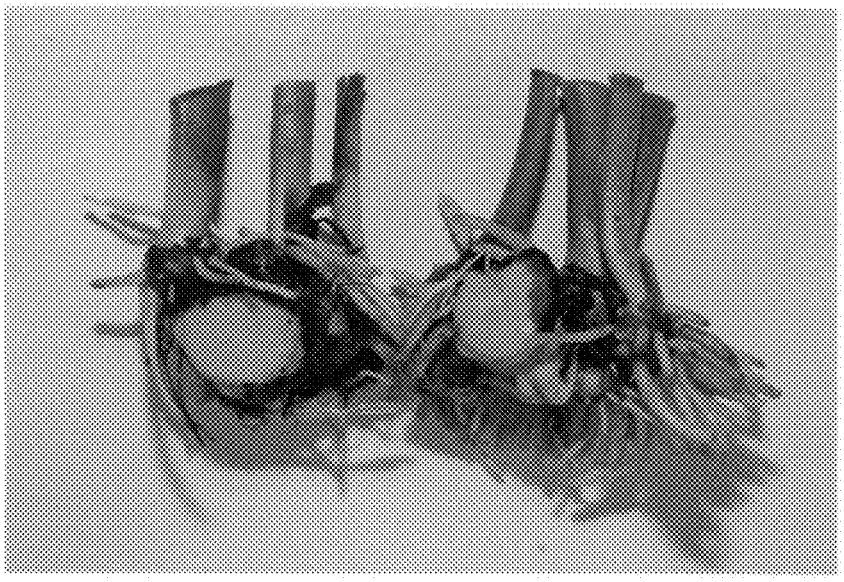
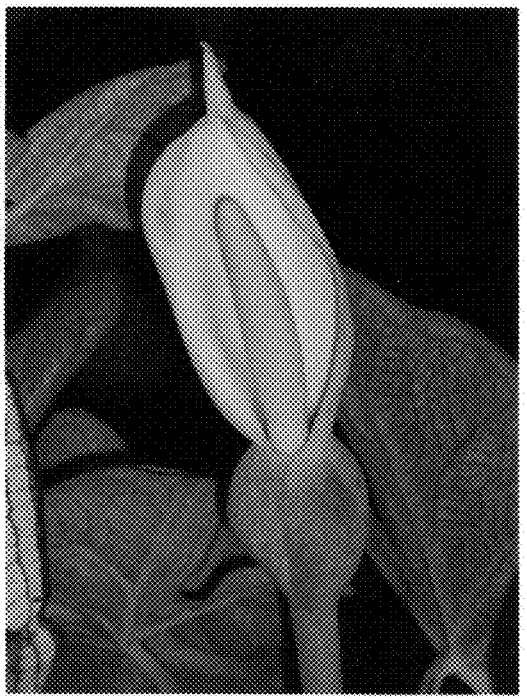

* * * * *